United States Patent
Chau et al.

(10) Patent No.: US 9,592,251 B2
(45) Date of Patent: Mar. 14, 2017

(54) MULTI-VINYLSULFONE CONTAINING MOLECULE

(75) Inventors: Ying Chau, Hong Kong (CN); Yu Yu, Hong Kong (CN)

(73) Assignee: THE HONG KONG UNIVERSITY OF SCIENCE AND TECHNOLOGY, Hong Kong (CN)

( * ) Notice: Subject to any disclaimer, the term of this patent is extended or adjusted under 35 U.S.C. 154(b) by 0 days.

(21) Appl. No.: 14/126,725

(22) PCT Filed: Jun. 15, 2012

(86) PCT No.: PCT/CN2012/000827
§ 371 (c)(1),
(2), (4) Date: Apr. 9, 2014

(87) PCT Pub. No.: WO2012/171335
PCT Pub. Date: Dec. 20, 2012

(65) Prior Publication Data
US 2014/0212373 A1    Jul. 31, 2014

Related U.S. Application Data

(60) Provisional application No. 61/457,837, filed on Jun. 16, 2011, provisional application No. 61/457,836, filed on Jun. 16, 2011.

(51) Int. Cl.
| | | |
|---|---|---|
| *A61K 9/14* | (2006.01) | |
| *A61K 39/29* | (2006.01) | |
| *A61K 31/74* | (2006.01) | |
| *A61K 31/715* | (2006.01) | |
| *A61K 31/795* | (2006.01) | |
| *A61K 31/573* | (2006.01) | |
| *C07K 16/22* | (2006.01) | |
| *A61K 31/10* | (2006.01) | |
| *A61K 31/721* | (2006.01) | |
| *A61K 31/728* | (2006.01) | |
| *A61K 31/734* | (2006.01) | |

(52) U.S. Cl.
CPC ............ *A61K 31/795* (2013.01); *A61K 31/10* (2013.01); *A61K 31/573* (2013.01); *A61K 31/721* (2013.01); *A61K 31/728* (2013.01); *A61K 31/734* (2013.01); *C07K 16/22* (2013.01)

(58) Field of Classification Search
None
See application file for complete search history.

(56) References Cited

U.S. PATENT DOCUMENTS

| | | |
|---|---|---|
| 4,582,865 A | 4/1986 | Balazs et al. |
| 5,900,461 A | 5/1999 | Harris |
| 6,958,212 B1 | 10/2005 | Hubbell et al. |
| 7,214,366 B2 | 5/2007 | Harris |
| 7,413,739 B2 | 8/2008 | Hubbell et al. |
| 7,744,912 B1 | 6/2010 | Hubbell et al. |
| 7,829,118 B1 | 11/2010 | Gravett et al. |
| 2008/0132444 A1 | 6/2008 | Li et al. |
| 2010/0015158 A1 | 1/2010 | Robinson et al. |
| 2010/0098772 A1 | 4/2010 | Robinson et al. |
| 2010/0272805 A1* | 10/2010 | Singh ........................ A61K 9/06 424/484 |
| 2014/0221307 A1 | 8/2014 | Gravett et al. |

FOREIGN PATENT DOCUMENTS

| | | |
|---|---|---|
| WO | WO-00/78285 A1 | 12/2000 |
| WO | WO/0078285 A1 | 12/2000 |
| WO | WO/2011-014432 A1 | 2/2011 |
| WO | WO-2011/014432 A1 | 2/2011 |

OTHER PUBLICATIONS

Google NPL Search for the term "gelatation"; 2-pages; downloaded Aug. 25, 2014.*
Tan et al.; Materials (2010) 3: 1746-1767; published Mar. 10, 2010.*
U.S. Documents—None.*
Non Patent Documents—None.*
International Search Report in International Application No. PCT/CN2012/000827, filed Jun. 15, 2012.
Morpurgo, M., et al., "Preparation and characterization of poly(ethylene glycol) vinyl sulfone." *Bioconjugate Chem*, 7, 363-368 (1996).
Lutolf, M.P. et al., "Synthesis and physicochemical characterization of end-linked poly(ethylene glycol)-co-peptide hydrogels formed by Michael-type addition." *Biomacromolecules*, 4, 713-722 (2003).
Lutolf, M.P. et al., "Synthetic matrix metalloproteinase-sensitive hydrogels for the conduction of tissue regeneration: Engineering cell-invasion characteristics." *P Natl Acad Sci USA*, 100, 5413-5418 (2003).
Lutolf, M.P., et al., "Cell-responsive synthetic hydrogels." *Adv Mater*, 15, 888-+ (2003).
Zisch, A. H., et al., "Cell-demanded release of VEGF from synthetic, biointeractive cell ingrowth matrices for vascularized tissue growth." *FASEB J.*, 17, 2260-2 (2003).

(Continued)

*Primary Examiner* — Jeffrey T Palenik

(74) *Attorney, Agent, or Firm* — Saliwanchik, Lloyd & Eisenschenk

(57) ABSTRACT

A multi-vinylsulfone containing molecule is described herein. The multi-vinylsulfone containing molecule can be formed by dissolving a water soluble polymer containing a hydroxyl group in an aqueous solution to form a polymer solution; adding a molecule containing two vinylsulfone groups to the polymer solution; and forming a modified polymer by controlling a number of the vinylsulfone groups that are added to the polymer. A hydrogel is also described herein that can include the multi-vinylsulfone containing molecule and a multi-thiol containing molecule. The hydrogel can be formed from an aqueous solution that includes the multi-vinylsulfone containing molecule and the multi-thiol containing molecule by undergoing gelatation upon delivery to a site in the body. Also described is a drug delivery system that employs the hydrogel.

20 Claims, 12 Drawing Sheets

(56) References Cited

OTHER PUBLICATIONS

Van De Wetering, P., et al., "Poly(ethylene glycol) hydrogels formed by conjugate addition with controllable swelling, degradation, and release of pharmaceutically active proteins." *J Control Release*, 102, 619-627 (2005).

Mather, B.D., et al., "Michael addition reactions in macromolecular design for emerging technologies." *Prog Polym Sci*, 31, 487-531 (2006).

Hiemstra, C., et al., "Release of model proteins and basic fibroblast growth factor from in situ forming degradable dextran hydrogels." *J. Control. Release*, 122, 71-8 (2007).

Park, K.D., et al., "Vinyl Sulfone-Terminated PEG-PLLA Diblock Copolymer for Thiol-Reactive Polymeric Micelle." *Macromolecules*, 42, 3437-3442 (2009).

Lajavardi, L., et al., "New formulation of vasoactive intestinal peptide using liposomes in hyaluronic acid gel for uveitis." *J. Control. Release*, 139, 2-30 (2009).

Jin, R. et al., "Synthesis and characterization of hyaluronic acid-poly(ethylene glycol) hydrogels via Michael addition: An injectable biomaterial for cartilage repair." *Acta Biomater*, 6, 1968-1977 (2010).

Kong, J.H., et al., "Long acting hyaluronate—exendin 4 conjugate for the treatment of type 2 diabetes." *Biomaterials*, 31, 4121-4128 (2010).

Oh, E.J. et al., "Target specific and long-acting delivery of protein, peptide, and nucleotide therapeutics using hyaluronic acid derivatives." *J Control Release*, 141, 2-12 (2010).

* cited by examiner

| pH-controlled modification | | | |
|---|---|---|---|
| Reaction pH | 5 | 9 | 10 |
| Degree of modification | 0% | 3% | 55% |
| Time-controlled modification (0.01 M NaOH) | | | |
| Reaction time | 2 min | 5 min | 15 min |
| Degree of modification | 5% | 13% | 25% |
| Time-controlled modification (0.1 M NaOH, 1.25x DVS) | | | |
| Reaction time | 1 min | 4 min | 8 min |
| Degree of modification | 12% | 25% | 38% |
| Time-controlled modification (0.1 M NaOH, 2.5x DVS) | | | |
| Reaction time | 1 min | 4 min | 8 min |
| Degree of modification | 24% | 48% | 70% |
| Time-controlled modification (0.1 M NaOH, 10x DVS) | | | |
| Reaction time | | 3 min | 6.5 min |
| Degree of modification | | 91% | 160% |

FIG. 12

MULTI-VINYLSULFONE CONTAINING MOLECULE

CROSS REFERENCE TO RELATED APPLICATIONS

This application claims priority to US provisional application No. 61/457,836, filed on Jun. 13, 2011 and to US provisional application No. 61/457,837, filed on Jun. 13, 2011.

TECHNICAL FIELD

This disclosure generally relates to generation of a multi-vinylsulfone molecule and to applications of the multi-vinylsulfone containing molecule.

BACKGROUND

Many polymers used in biomedical applications are hydroxyl-bearing water soluble polymers. Examples of hydroxyl-bearing water soluble polymers include: hyaluronic acid (HA), polyethylene glycol (PEG), dextran, polyvinyl alcohol, alginate, cyclodextrin, and the like. Hydroxyl-bearing water soluble polymers are generally non-toxic, and the hydroxyl groups generally allow these polymers to be soluble in an aqueous environment. However, hydroxyl-bearing water soluble polymers alone do not usually have functionality toward animal cells or tissues and must be modified with an active agent to exhibit functionality toward animal cells or tissues.

For example, hydroxyl-bearing water soluble polymers can be linked with hydrophobic anti-cancer drugs to increase the solubility and targeting of the anticancer drug. Hydroxyl-bearing water soluble polymers can be linked with proteins or other labile biomolecules to increase the half life of a drug in circulation. Other examples include making nanoparticles and imaging agents. The hydroxyl-bearing water soluble polymer can also be modified for use as a hydrogel. A hydrogel made with a modified hydroxyl-bearing water soluble polymer can be used, for example, in a tissue engineering scaffold, a drug delivery depot, a drug carrier in polymer-drug conjugates, as well as other biomedical applications. Modifying hydroxyl-bearing water soluble polymers for use in a hydrogel traditionally involves complicated chemistry and harsh conditions, which may be expensive and not suitable for biomedical applications.

The above-described background is merely intended to provide an overview of contextual information regarding hydroxyl-bearing water soluble polymers, and is not intended to be exhaustive. Additional context may become apparent upon review of one or more of the various non-limiting embodiments of the following detailed description.

SUMMARY

The following presents a simplified summary of the specification in order to provide a basic understanding of some aspects of the specification. This summary is not an extensive overview of the specification. It is intended to neither identify key or critical elements of the specification nor delineate any scope of particular embodiments of the specification, or any scope of the claims. Its sole purpose is to present some concepts of the specification in a simplified form as a prelude to the more detailed description that is presented later.

In accordance with one or more embodiments and corresponding disclosure, various non-limiting aspects are described in connection with a hydroxyl-bearing water soluble polymer modified with two or more vinylsulfone groups. The modified polymer can be combined with an active agent and/or form crosslinks between polymers at in aqueous medium at mild physiological conditions of a pH of about 7.4, a pressure of about 1 atm, or a temperature of about 37 degrees Celsius.

A method of forming the modified polymer is described, according to an embodiment. A water soluble polymer containing a hydroxyl group is dissolved in an aqueous solution to form a polymer solution. A molecule containing two vinylsulfone groups is added to the polymer solution. The modified polymer is formed by controlling a number of the vinylsulfone groups that are grafted to the polymer. The vinylsulfone groups are chemically reactive.

According to another embodiment, a hydrogel that can be made from the modified polymer is described. The hydrogel includes the modified polymer (a multi-vinylsulfone containing molecule) and a multi-thiol containing molecule. The hydrogel is formed at a site of a biological tissue upon delivery to the site. The hydrogel is formed from an aqueous solution that includes the modified polymer and the multi-thiol containing molecule by a covalent bond between the modified polymer and the multi-thiol containing molecule.

In a further embodiment, a drug delivery system is described. The drug delivery system includes the modified polymer (a multi-vinylsulfone containing molecule), a multi-thiol containing molecule and a therapeutic molecule. The drug delivery system dissolves in water to form an aqueous solution, which undergoes gelation upon administration to a site in a body.

The following description and the drawings set forth certain illustrative aspects of the specification. These aspects are indicative, however, of but a few of the various ways in which the various embodiments of the specification may be employed. Other aspects of the specification will become apparent from the following detailed description of the specification when considered in conjunction with the drawings.

BRIEF DESCRIPTION OF THE DRAWINGS

Numerous aspects and embodiments are set forth in the following detailed description, taken in conjunction with the accompanying drawings, in which like reference characters refer to like parts throughout, and in which:

FIG. 12 is an exemplary non-limiting table illustrating the degree of modification of hyaluronic acid with vinylsulfone using different synthesis methods, according to an embodiment;

DETAILED DESCRIPTION

Figure 1:
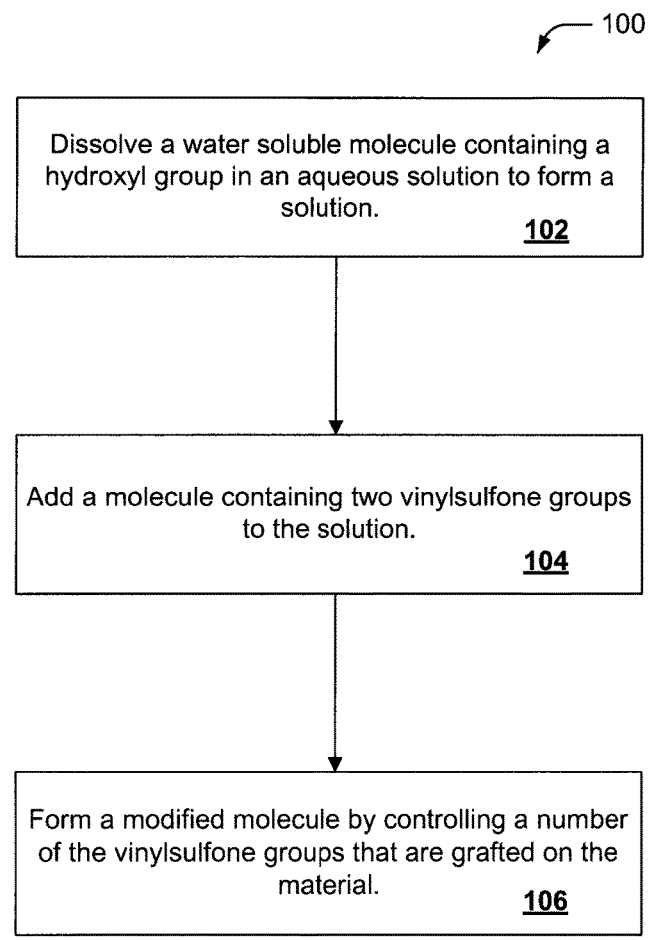
FIG. 1 is an exemplary non-limiting process flow diagram of a method for generating a functional vinylsulfone group, a hydroxyl-bearing molecule, according to an embodiment.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that the certain aspects of disclosure may be practiced without these specific details, or with other methods, components, molecules, etc. In other instances, well-known structures and devices are shown in block diagram form to facilitate description and illustration of the various embodiments.

In accordance with one or more embodiments described in this disclosure, described herein is a multi-vinylsulfone molecule: a multi hydroxyl-bearing water soluble molecule modified with two or more vinylsulfone groups. The multi-vinylsulfone containing molecule can be formed by dissolving a water soluble molecule containing a hydroxyl group in an aqueous solution to form a solution; adding a molecule containing two vinylsulfone groups to the solution; and forming a modified molecule by controlling a number of the vinylsulfone groups that are added to the molecule. Also described are applications of the multi-vinylsulfone containing molecule, including a hydrogel and a drug delivery system employing the hydrogel. The hydrogel includes the multi-vinylsulfone containing molecule and a multi-thiol containing molecule and can be formed from an aqueous solution that includes the multi-vinylsulfone containing molecule and the multi-thiol containing molecule that undergoes gelation upon delivery to a site in the body. The multi-vinylsulfone containing molecule is active toward the multi-thiol containing molecule at mild aqueous conditions.

Referring now to the drawings, with reference initially to FIG. 1, illustrated is an exemplary non-limiting process flow diagram of a method 100 for generating a functional vinylsulfone group, a hydroxyl-bearing molecule, according to an embodiment. Method 100 allows for simple, efficient and controllable modification of a hydroxyl-bearing molecule with a functional vinylsulfone group.

Method 100 takes place in an aqueous environment ("aqueous solution") to maximize the yield and/or minimize the potential hazard when the modified molecule is used in a biological system. At element 102, a water soluble molecule containing a hydroxyl group is dissolved in an aqueous solution to form a solution. The aqueous solution, in an embodiment, is an alkaline aqueous solution. The alkaline aqueous solution can have a pH greater than 7. In an embodiment, the alkaline aqueous solution has a pH from about 8 to about 15. According to another embodiment, the water soluble molecule containing the hydroxyl group is dissolved in the aqueous solution with a pH of about 7 and after the water soluble molecule containing the hydroxyl group is dissolved, the pH of the solution is adjusted to be alkaline.

The aqueous solution can include a salt, an aqueous solvent, any other molecule that regulates the pH of the solution, any other molecule that facilitates the modification, or any other molecule that minimizes the potential hazard when the modified molecule is used in a biological system.

According to an embodiment, the water soluble molecule containing a hydroxyl group is a water soluble polymer containing a hydroxyl group. Examples of a water soluble polymer containing a hydroxyl group (or hydroxyl-containing water soluble polymers) include: hyaluronic acid (HA), polyethylene glycol (PEG), dextran, polyvinyl alcohol (PVA), alginate, cyclodextrin, and the like.

The modification is a simple and efficient process. At element 104, a molecule containing two vinylsulfone groups is added to the solution. An example of a molecule containing two vinylsulfone groups is divinylsulfone (DVS). At element 106, a modified molecule is formed by controlling a number of the vinylsulfone groups that are added to the molecule. The modified molecule is formed by a one-step process using water as the solvent. At a high pH (alkaline, pH greater than about 7), the dissolved molecule containing hydroxyl is reactive to the molecule containing at least two vinylsulfone groups. The vinylsulfone groups are added to the molecule when the dissolved molecule reacts with molar excess of the molecule containing two vinylsulfone groups. In an embodiment, the modified molecule is biocompatible.

The vinylsulfone groups grafted on the modified molecule are active and chemically reactive with a counterpart. In an embodiment, the counterpart is a molecule containing a nucleophile. The vinylsulfone groups can covalently bond to the nucleophile. Examples of nucleophiles include thiols and amines.

Figure 2:
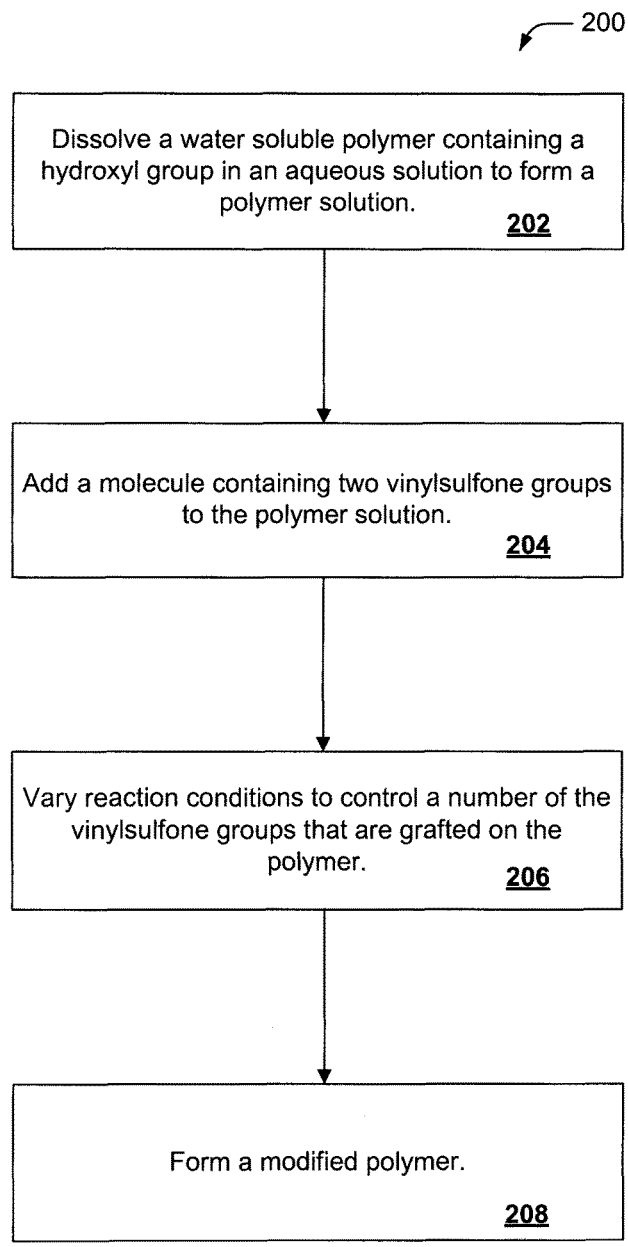
FIG. 2 is an exemplary non-limiting process flow diagram of a method for controlling a number of vinylsulfone groups that are grafted on a hydroxyl-bearing polymer, according to an embodiment.

Referring now to FIG. 2, illustrated is an exemplary non-limiting process flow diagram of a method 200 for controlling a number of vinylsulfone groups that are grafted on a hydroxyl-bearing polymer, according to an embodiment. At element 202, a water soluble polymer containing a hydroxyl group is dissolved in an aqueous solution to form a polymer solution. The water soluble polymer containing a hydroxyl group can be any polymer that is water soluble and contains one or more hydroxyl groups. Examples of a water soluble polymer containing a hydroxyl group include: hyaluronic acid (HA), polyethylene glycol (PEG), dextran, polyvinyl alcohol (PVA), alginate, cyclodextrin, and the like.

At element 204, a molecule containing two vinylsulfone groups is added to the polymer solution. An example of a molecule containing two vinylsulfone groups is divinylsulfone. The aqueous solution and/or the polymer solution is alkaline. According to an embodiment, the alkaline solution has a pH greater than about 7. In another embodiment, the alkaline solution has a pH from about 8 to about 15. According to a further embodiment, the alkaline solution has a pH from about 11.5 to about 16. In another embodiment, the alkaline solution has a pH from about 11.5 to about 14.5.

At element 206, reaction conditions are varied to control a number of the vinylsulfone groups that are grafted on the polymer or a degree of modification of the polymer. According to an embodiment, the degree of modification can be controlled over a wide range. Examples of different mechanisms for controlling the number of vinylsulfone groups that are added to the molecule include: varying a reaction time, varying a reaction pH, varying an amount of molecules containing two vinylsulfone groups, varying a molar ratio between the vinylsulfone groups and the hydroxyl groups, varying a basicity of the aqueous solution, or the like. At element 208, the modified polymer is formed.

In an embodiment, the water soluble molecule containing a hydroxyl group is hyaluronic acid. Hyaluronic acid is a polymer that contains four hydroxyl groups per disaccharide unit. Hyaluronic acid is reactive toward divinylsulfone at a high pH. For example, hyaluronic acid is reactive toward divinylsulfone at a pH greater than about 11.5. In an embodiment, hyaluronic acid is reactive toward divinylsulfone at a pH from about 12 to about 14.5. In another embodiment, hyaluronic acid is reactive toward divinylsulfone at a pH of about 13.3.

The pKa of hydroxyl groups in saccharides is from about 12 to about 13. Accordingly, in a high pH environment (greater than about 11.5), most of the hydroxyl groups are deprotonated and become an alkoxide ion ($RO^-$). Being an active nucleophile, the alkoxide ion can form a covalent linkage with the electrophilic double bond of vinylsulfone by 1,4-nucleophillic conjugate addition (Michael-type addition).

The Michael-type addition reaction has been previously used to cross link hyaluronic acid with divinylsulfone. In cross linking, the molar ratio of divinylsulfone to hydroxyl is low (e.g., 1:4), such that both vinylsulfone groups of each divinylsulfone react with hydroxyl groups of hyaluronic acid and crosslink the hyaluronic acid chains. Crosslinking can be avoided if the vinylsulfone groups of the divinylsulfone are in excess to the hydroxyl groups from the hyaluronic acid (the divinylsulfone to hydroxyl molar ratio is increased). The reaction can be further controlled by optimizing reaction parameters, including, for example, pH and time. The result is that divinylsulfone is not used as a crosslinker, but as a reagent to modify polymers by a simple "click" reaction.

Stoichiometrically, only one vinylsulfone group of each divinylsulfone molecule will react with the OH group of the hyaluronic acid. The other vinylsulfone group will remain unreacted. The remaining vinylsulfone groups can be used, for example, as in situ crosslinking points or protein conjugation points in a subsequent "click" reaction.

A "click" reaction is a reaction tailored to generate substances quickly and reliably by joining small (modular) units together. A "click" reaction is modular, is wide in scope, gives high chemical yields, generates inoffensive byproducts, is stereospecific, is physiologically stable, exhibits a large thermodynamic force (greater than about 84 kJ/mol) to favor a reaction with a single reaction product, and has a high atom economy. Preferably, a "click" reaction has simple reaction conditions, uses readily available starting materials and reagents, uses no solvent or uses a solvent that is benign or easily removed (water), and provides simple product isolation by non-chromatographic means.

Additionally, the method for synthesizing the modified polymers is a simple "click" method. This simple "click" method enables the modified polymers to become "clickable" subsequently under physiological conditions. The modified polymers, instead of forming pre-crosslinked hydrogels, generate "clickable" precursors that are suitable for a wide range of biomedical uses. Examples of biomedical uses include drug delivery and tissue engineering.

Figure 3:
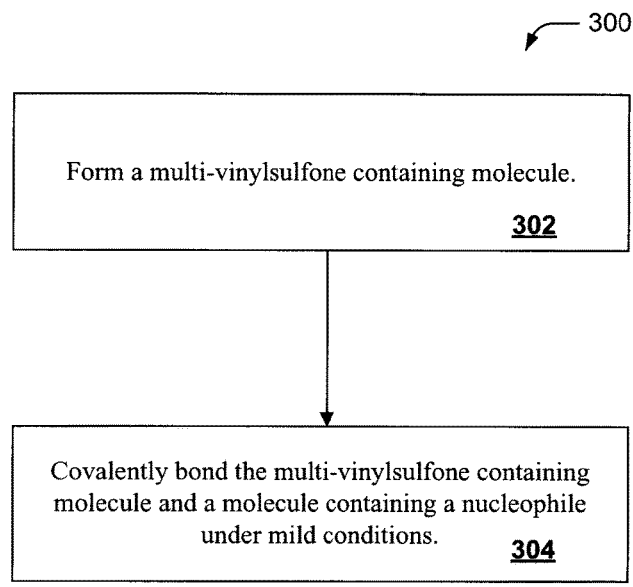
FIG. 3 is an exemplary non-limiting process flow diagram of a nucleophile-Michael addition process, according to an embodiment.

Referring now to FIG. 3, illustrated is an exemplary non-limiting process flow diagram of a nucleophile-Michael addition process 300, according to an embodiment. At element 302, a multi-vinylsulfone containing molecule is formed. At element 304, the multi-vinylsulfone containing molecule and a molecule containing a nucleophile are covalently bonded under mild physiological conditions. In an embodiment, mild physiological conditions refer to a pH from about 5 to about 9, a temperature from about 10 to about 40 degrees Celsius, or a water content of at least about 90%. In another embodiment, mild physiological conditions refer to a pH of about 7.4, a pressure of about 1 atm, a temperature of about 37 degrees Celsius, or a water content of at least about 99%. Examples of nucleophiles are amines and thiols.

In an embodiment, the multi-vinylsulfone containing molecule is a multi-vinylsulfone functionalized polymer and the nucleophile is a thiol. The multi-vinylsulfone functionalized polymer can participate in a subsequent thiol-Michael addition reaction with a thiol counterpart. The thiol-Michael addition reaction occurs between electrophilic double bonds and thiols. At physiological pH, thiols are partially deprotonated and become thiol anions ($S^-$, Michael acceptors), which can readily react with certain electron-deficient double bonds, such as the double bonds of the vinylsulfone groups (Michael acceptor). The reaction between the vinylsulfone groups and the thiols is compatible to proteins, cells, and other biological structures.

Figure 4:
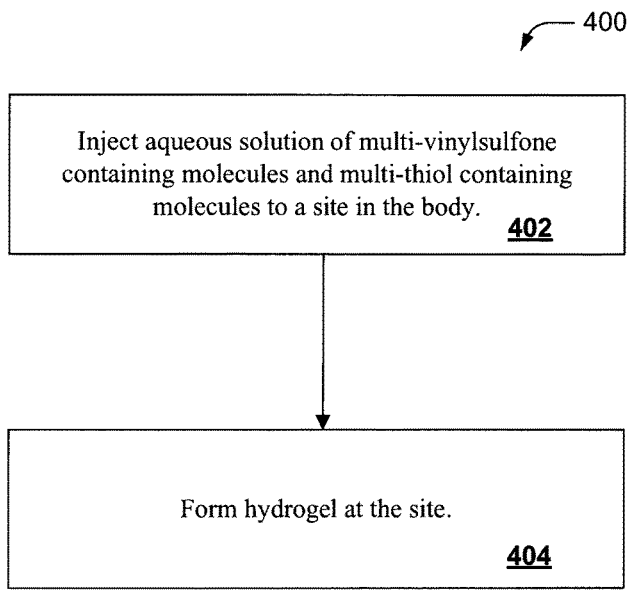
FIG. 4 is an exemplary non-limiting process flow diagram of a method for forming a hydrogel, according to an embodiment.

The click reaction between the vinylsulfone groups and the thiols is conducive to forming a hydrogel. The hydrogel includes the multi-vinylsulfone containing molecule and the multi-thiol containing molecule. Referring now to FIG. 4, illustrated is a non-limiting process flow diagram of a method 400 for synthesizing a hydrogel. At element 402, an aqueous solution of the multi-vinylsulfone containing molecule and the multi-thiol containing molecule is injected into a site in the body. The multi-vinylsulfone containing molecule can be a water soluble polymer containing hydroxyl groups modified with vinylsulfone functional groups according to methods 100 or 200 and the multi-thiol containing molecule containing thiol. According to an embodiment, the multi-thiol containing molecule is a polymer containing at least two thiol groups. In a further embodiment, the multi-vinylsulfone containing molecule and/or the multi-thiol containing molecule is a polysaccharide derivative.

At element 404, the hydrogel is formed at the site from the aqueous solution by covalently bonding the multi-vinylsulfone containing molecule and the multi-thiol containing molecule. The aqueous solution can also include free vinylsulfone groups and/or thiol groups that can interact with therapeutics or with biological tissue. The free vinylsulfone groups and/or thiol groups can be modulated by a modulator molecule. The aqueous solution, in another embodiment, can also include a salt, an organic solvent, a therapeutic agent or a modulator molecule.

Figure 5:
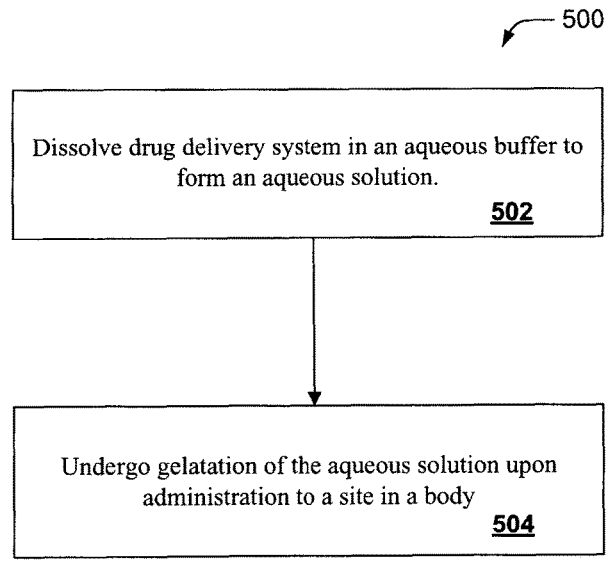
FIG. 5 is an exemplary non-limiting process flow diagram of a method for administering a drug delivery system, according to an embodiment.

The hydrogel can be used in many applications, including a drug delivery system. FIG. 5 is an exemplary non-limiting process flow diagram of a method 500 for administering a drug delivery system, according to an embodiment. The drug delivery system of method 500 employs polymers that can undergo in situ gelatation after injection to the body. Examples of polymers that can undergo in situ gelation upon injection in the body are a multi-vinylsulfone containing molecule and a multi-thiol containing molecule. The multi-vinylsulfone containing molecule can be derived from a water soluble hydroxyl containing material according to methods 100-300. In an embodiment, the multi-vinylsulfone containing molecule and/or the multi-thiol containing molecule are polymers. The polymers can be polysaccharide derivatives.

The drug delivery system also includes a therapeutic molecule ("drug"). Examples of therapeutic molecules include: biomacromolecules (e.g., proteins, peptides, nucleic acids, aptamers, etc.), particulated small molecular drugs, or particles encapsulating the particulated small molecular drugs. In an embodiment, the therapeutic molecules can include any therapeutic molecule that can be used to treat a posterior eye condition, including age-related macular degeneration and diabetic retinopathy.

According to method 500, at element 502, the drug delivery system, including the multi-vinylsulfone containing molecule and a multi-thiol containing molecule and the therapeutic molecule are dissolved in an aqueous buffer to form an aqueous solution. In an embodiment, the aqueous buffer is water. At element 504, the aqueous solution undergoes gelation upon administration to a site in a body. In an embodiment, the site in the body is a surface of the body or an interior of the body. In a further embodiment, the site is the posterior of the eye.

The aqueous solution is administered to the site, in an embodiment, by injection. The aqueous solution can be easily injected to the site, even with a small needle, so that the therapeutic material can be placed at the targeted position with minimum impact on surrounding tissues. The injection can be an injection to the surface of the body or to an interior of the body. Example types of injection include: intravitrial injection, peribulbar injection, sub-Tenon injection, or the like. When the site is the eye, the needle for the injection can be, for example, 31 gauge so that the therapeutics can be placed at a targeted position with minimum impact on the surrounding ocular tissues.

The aqueous solution can undergo gelation when the multi-vinylsulfone containing molecule forms a covalent bond with the multi-thiol containing molecule. The covalently bonded multi-thiol containing molecule and multi-vinylsulfone containing molecule can form a hydrogel according to method 400.

The multi-vinylsulfone containing molecule and the multi-thiol containing molecule are crosslinked after injection into hydrophilic chains. The crosslinked hydrophilic chains can encapsulate the therapeutic molecule. The therapeutic molecule is encapsulated within a network formed by the multi-vinylsulfone containing molecule and the multi-thiol containing molecule. The crosslinked network protects the therapeutic molecule from digestion by enzymes and avoids the therapeutic molecule contacting tissues. Moreover, according to an embodiment, different types of therapeutic materials (for example, biomacromolecule and small molecule encapsulated particles) can be encapsulated in the same in situ hydrogel, by which controlled-combination therapy can be achieved.

The hydrogel has an aqueous environment inside. For labile biomolecues, the aqueous environment inside the hydrogel versus a hydrophobic environment inside a traditional polymer implant enables the labile biomolecules to maintain correct three-dimensional structure and enhances stability of the labile biomolecules and helps to maintain therapeutic efficacy of the labile biomolecules. Similarly, drug encapsulating particles, after being encapsulated in the hydrogel, will not contact the blood/lymphatic system, reducing the chance of being eliminated. In the eye, this encapsulation also reduces the risk of elicit adverse effects, such as sterile endophalmitis by contacting ocular tissue.

The hydrogel formation and therapeutic molecule encapsulation occur at mild physiological conditions. In an embodiment, mild physiological conditions refer to a pH from about 5 to about 9, a temperature from about 10 to about 40 degrees Celsius, or a water content of at least about 90%. In another embodiment, mild physiological conditions refer to a pH of about 7.4, a pressure of about 1 atm, a temperature of about 37 degrees Celsius, or a water content of at least about 99%.

The hydrogel drug delivery system can facilitate controlled drug delivery to the site. The hydrogel drug delivery system is useful for prolonged delivery of therapeutics to the site. Therapeutics can be delivered to the site for days, months or years. Because of the in situ gelation property of the hydrogel, the release rate of the therapeutic molecule can be controlled, for example, by controlling the crosslinking density. Additionally, the release rate can be further controlled by selecting different polymers for the release of different drugs. For example, when long term release is desirable, a positively charged drug, like Avastin, can be better trapped in a negatively charged polymer, like multi-vinylsulfone hyaluronic acid.

Figure 6:
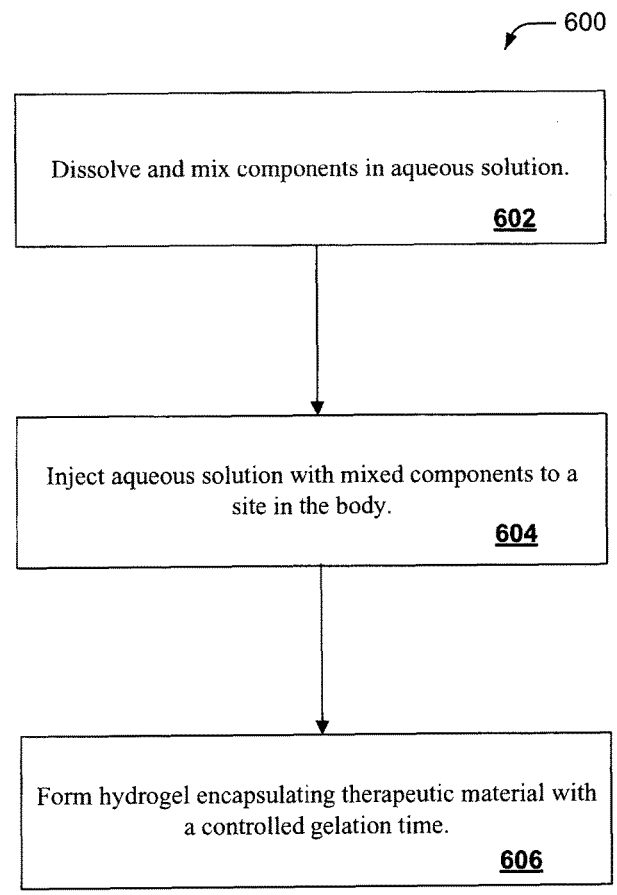
FIG. 6 is an exemplary non-limiting process flow diagram of a method for forming a hydrogel encapsulating a therapeutic material at a site in the body, according to an embodiment.

Referring now to FIG. 6, illustrated is an exemplary non-limiting process flow diagram of a method 600 for forming a hydrogel encapsulating a therapeutic material at a site in the body, according to an embodiment. Method 600 refers to an in situ forming hydrogel formulation for controlled delivery of therapeutics to a site in the body. In an embodiment, the therapeutics are macromolecule and/or small molecular therapeutics and the site the body is the eye.

At element 602, components are dissolved and mixed in an aqueous solution. The components include polymers with multiple vinylsulfone groups per molecule formed according to methods 100-300, molecules having multiple thiols per molecule, and therapeutic molecules and/or therapeutic molecule-encapsulated particles.

At element 604, the aqueous solution with the mixed components is injected to a site in the body. According to an embodiment, the site in the body is the eye. After injection the polymers with multiple vinylsulfone groups per molecule formed according to methods 100-300 and the molecules having multiple thiols per molecule are crosslinked and the therapeutic material is encapsulated within the crosslinked network at mild physiological conditions. At element 606, a hydrogel is formed that encapsulates the therapeutic material with a controlled gelation time. The formation and encapsulation are each in situ processes. The gelation time is well controlled so that the hydrogel is completely formed shortly after injection, but not too fast to allow manipulation of the therapeutic material. In an embodiment, the gelation time sufficient to allow complete encapsulation of the therapeutic material, but shorter than a time of elimination of the free therapeutic material via circulation of the blood or lymph.

EXPERIMENTAL

The following examples illustrate modification of hyaluronic acid, dextran, polyvinyl alcohol, alginate and polyethylene glycol with vinylsulfone groups. However, it should be noted that the methods 100-600 are not limited to merely these polymers; instead, methods 100-600 are applicable to all hydroxyl containing water soluble polymers. The values of reaction variables, such as, the concentration of the polymers, pH, vinylsulfone to hydroxide ratio, and the like, and/or the protocols of the method, such as, the purification procedure, choice of polymer, choice of thiol containing molecules, reaction time, reaction buffer, and the like can be changed to control the addition of vinylsulfone groups to the polymers in the formation of the modified polymers. The vinylsulfone groups of the modified polymers can participate in a subsequent thiol-Michael "click" reaction with a thiol counterpart.

The following examples are exemplary or illustrative of the application of the principles described above. It will be noted that experimental data provided does not limit the scope of the embodiments. Rather, such data merely illustrate the preparation of composition embodiments in accordance with the subject innovation as well as for demonstrating the properties described above illustrating the usefulness of the composition for drug delivery.

Synthesis of Modified Molecule

Synthesis of Vinylsulfone-Modified Hyaluronic Acid

Hyaluronic acid was dissolved in 0.1 M NaOH at 2% w/v (corresponding to approximately 200 μmol hydroxyl groups per ml). Divinylsulfone was added into a vigorously vortexing hyaluronic acid solution in excess at a molar ratio of 1.25-times the hydroxyl groups of hyaluronic acid. The reaction was carried out for 10 minutes and stopped by adjusting the pH to 5 using 5M HCl. After adjusting the pH, the solution was purified by dialysis and freeze-dried.

Figure 7:
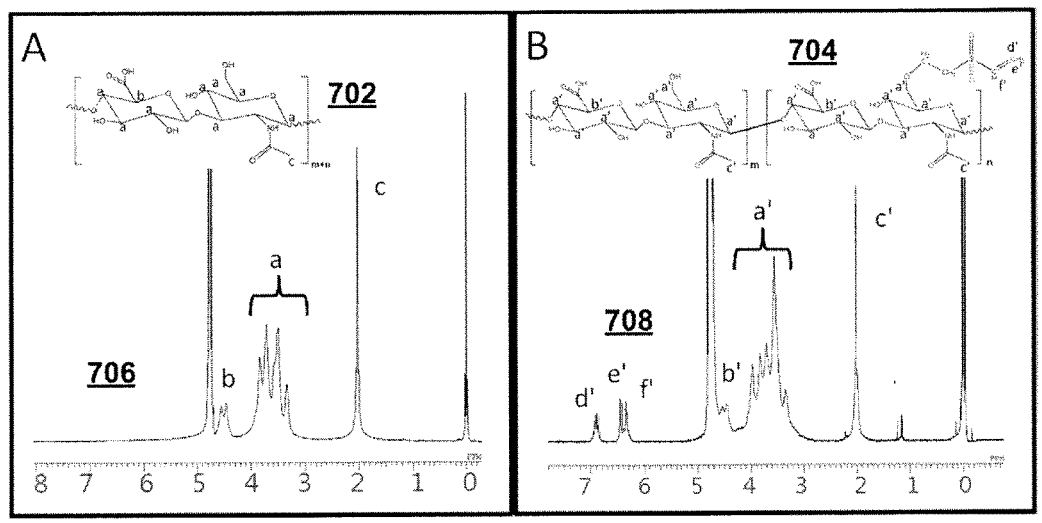
FIG. 7 is an exemplary non-limiting illustration of results of $^1$H NMR confirming modification of hyaluronic acid with vinylsulfone, according to an embodiment.

The success of conjugation was confirmed by $^1$H NMR, as shown in FIG. 7. FIG. 7(A) relates to unmodified hyaluronic acid and FIG. 7(B) relates to hyaluronic acid modified with vinylsulfone. Element 702 is an illustration of the chemical structure of unmodified hyaluronic acid and element 704 is an illustration of the chemical structure of hyaluronic acid modified with vinylsulfone. Element 706 is the $^1$H NMR spectrum of unmodified hyaluronic acid and element 708 is the $^1$H NMR spectrum of hyaluronic acid modified with vinylsulfone.

The NMR signals of free vinylsulfone double bonds are at $\delta=6.3$ (f'), 6.4 (e') and 6.9 (d') in element 708 of FIG. 7(B). The degree of modification, defined as the number of vinylsulfone groups divided by the number of disaccharide repeating units, was calculated from $^1$H NMR spectra by comparing the integral signals at $\delta=6.9$ and at $\delta=2$ (acetyl group of the disaccharide).

Synthesis of Vinylsulfone-Modified Dextran

Figure 8:
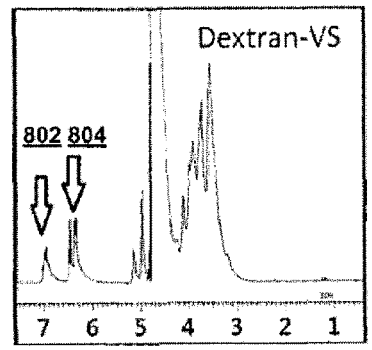
FIG. 8 is an exemplary non-limiting illustration of results of $^1$H NMR confirming modification of dextran with vinylsulfone, according to an embodiment.

Dextran was dissolved in 0.1 M NaOH by 2% w/v. A 1.5× excessive (molar ratio to hydroxyl groups of the polymer) divinylsulfone was added into a vigorously vortexing polymer solution. The reaction was stopped by adjusting the pH to 5 with 5M HCl. After the pH adjustment, the solution was purified by dialysis and freeze-dried. FIG. 8, elements 802 and 804, confirm the success of conjugation.

Synthesis of Vinylsulfone-Modified Polyvinyl Alcohol

Figure 9:
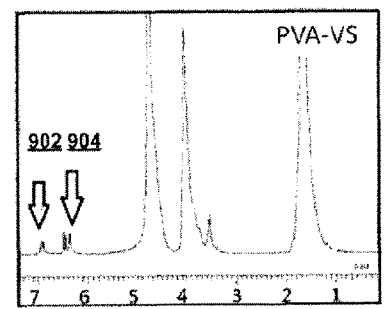
FIG. 9 is an exemplary non-limiting illustration of results of $^1$H NMR confirming modification of polyvinyl acetate with vinylsulfone, according to an embodiment.

Polyvinyl alcohol was dissolved in 0.1 M NaOH by 2% w/v. A 1.5-times excessive (molar ratio to hydroxyl groups of the polymer) divinylsulfone was added into a vigorously vortexing polymer solution. The reaction was stopped by adjusting the pH to 5 with 5M HCl. After the pH adjustment, the solution was purified by diafiltration and freeze-dried. FIG. 9, elements 902 and 904, confirm the success of conjugation.

Synthesis of Vinylsulfone-Modified Alginate

Figure 10:
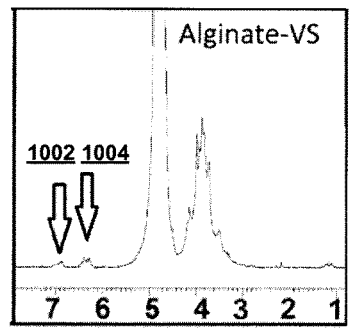
FIG. 10 is an exemplary non-limiting illustration of results of $^1$H NMR confirming modification of algenate with vinylsulfone, according to an embodiment.

Alginate was dissolved in 0.1 M NaOH by 2% w/v. A 1.5-times excessive (molar ratio to hydroxyl groups of the polymer) divinylsulfone was added instantly into the vigorously vortexing polymer solution. The reaction was stopped by adjusting the pH to 5 with 5M HCl. After the pH adjustment, the solution was purified by diafiltration and freeze-dried. FIG. 10, elements 1002 and 1004, confirm the success of conjugation.

Synthesis of Vinylsulfone-Modified Polyethylene Glycol

Figure 11:
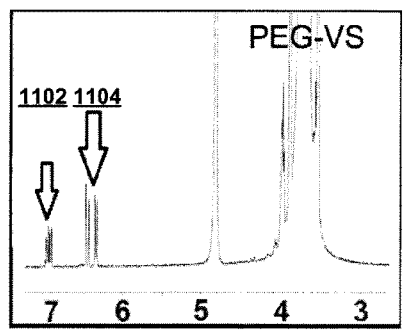
FIG. 11 is an exemplary non-limiting illustration of results of $^1$H NMR confirming modification of polyethylene glycol with vinylsulfone, according to an embodiment.

Polyethylene glycol was dissolved in 0.1 M NaOH by 6% w/v. A 10-times excessive (molar ratio to hydroxyl groups of the polymer) divinylsulfone was added into the vigorously vortexing polymer solution. The reaction was stopped by adjusting the pH to 5 with 5M HCl. After the pH adjustment, the solution was purified by diafiltration and freeze-dried. FIG. 11, elements 1102 and 1104, confirm the success of conjugation.

Controlling the Degree of Modification

The degree of modification of a certain hydroxyl containing water soluble polymer can be controlled by at least three factors: reaction pH, reaction time and the molar ratio between divinylsulfone and OH.

The following examples show how to control the degree of modification of hyaluronic acid and dextran; however, it should be noted that control principle is applicable to other hydroxyl containing water soluble polymers as well.

Controlling the Degree of Modification of Vinylsulfone-Modified Hyaluronic Acid

A hyaluronic acid solution was dissolved in nanopure Water® and adjusted to different pH values (in the range of 9 to 10) by drop-wise addition of 6 M NaOH. Divinylsulfone was added into the vigorously vortexing hyaluronic acid solution, at a molar ratio of 1.25-times in excess of the hydroxyl groups of hyaluronic acid.

The reaction was carried out for 12 hours and stopped by adjusting the pH to 5 using 5M HCl. For the time-controlled experiment, HA was dissolved in 0.01 M or 0.1 M NaOH solution at 2% w/v. Divinylsulfone was added into the vigorously vortexing hyaluronic acid solution at a molar ratio of 1.25-times the hydroxyl groups of hyaluronic acid. The reactions were stopped at predetermined time points by adjusting the pH to 5 using 5M HCl.

To investigate the changing molar ratio of divinylsulfone:OH, hyaluronic acid was dissolved in 0.1 M NaOH and divinylsulfone was added instantly into the vigorously vortexing hyaluronic acid solution at a molar ratio of 1.25, 2.5, or 10 times the hydroxyl groups of hyaluronic acid. The reactions were stopped at pre-determined time points by adjusting the pH to 5 using 5M HCl. After the pH adjustment, the solution was purified by diafiltration and freeze-dried.

Figure 13:
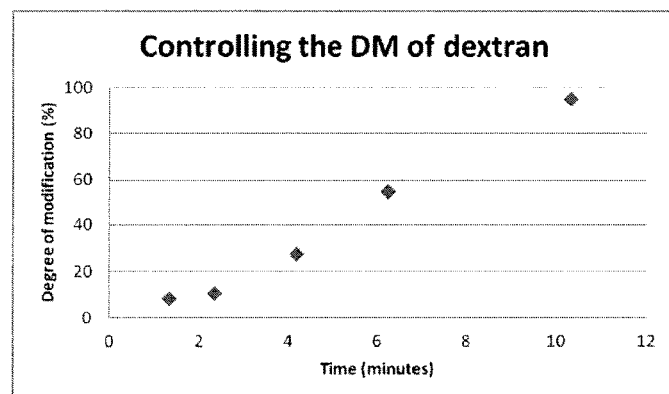
FIG. 13 is an exemplary non-limiting graph illustrating the degree of modification of dextran with vinylsulfone, according to an embodiment.

The success of conjugation and the degree of modification was examined by $^1$H NMR. A table illustrating the types of modification for hyaluronic acid is shown in FIG. 13. Vinylsulfone-modified hyaluronic acid with degrees of modification lower than 3% and as high as 160% was synthesized.

Controlling the Degree of Modification of Vinylsulfone-Modified Dextran

Dextran was dissolved in 0.025 M NaOH solution and 1.2-times divinylsulfone was added to the vigorously stirring dextran solution. The reactions were stopped at predetermined time points by adjusting the pH to 5 using 5M HCl. After the pH adjustment, the solution was purified by dialysis or diafiltration or other types of methods and freeze-dried. The success of conjugation and the DM was examined by $^1$H NMR, as illustrated in FIG. 13.

Cytotoxicity of Vinylsulfone-Modified Polymer

To examine whether a vinylsulfone group conjugated on a polymer is toxic to a cell, a Live/Death assay was used for testing cytotoxicity of vinylsulfone-modified hyaluronic acid.

Figure 14:
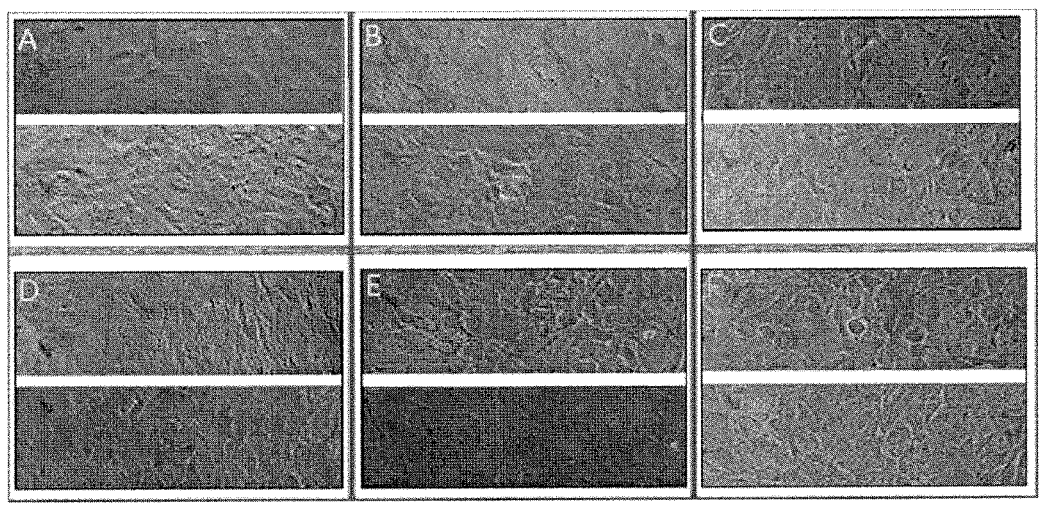
FIG. 14 shows exemplary non-limiting results of an assay showing that vinylsulfone-modified hyaluronic acid is not cytotoxic at various concentrations (0.1% to 1%) and at different incubation times (5 hours and 20 hours), according to an embodiment.

NIH 3T3 cells were cultured on a 96 well plate, and vinylsulfone-modified hyaluronic acid of concentration 0.1% to 1% was added to the cell and incubated for 5 hours or 20 hours before the assays were performed. As shown in FIG. 14, no cytotoxic effect were observed (in the assays, live cells appear green and dead cells appear red; no red was observed).

Reaction of Vinylsulfone-Modified Polymers with Thiols

The following examples demonstrated that the vinylsulfone modified polymers can react with thiol at mild aqueous conditions. Since these conditions are compatible with labile biomolecules, cells, animals and humans, the vinylsulfone modified polymers are excellent materials for preparing in situ hydrogel, polymer-drug conjugate, protein encapsulation, surface modification, or the like.

Figure 15:
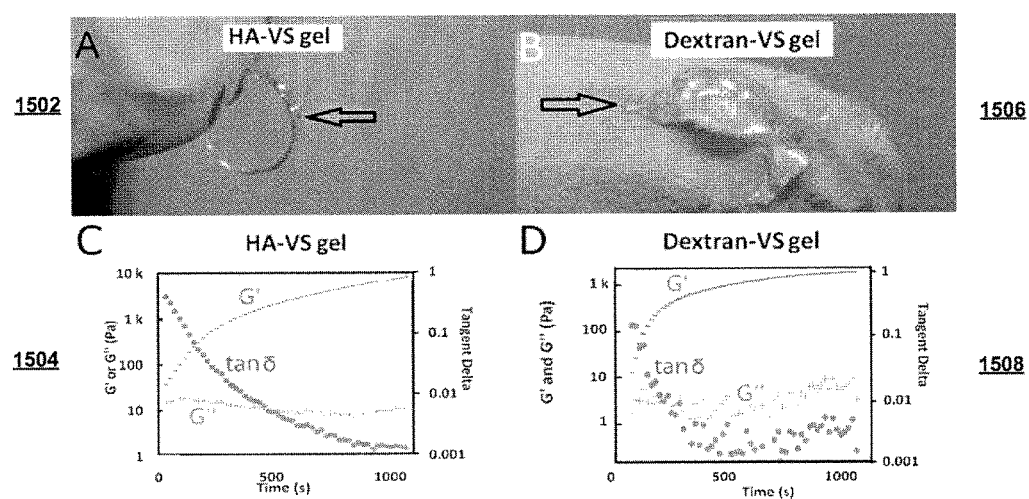
FIG. 15 shows exemplary non-limiting gelation kinetics and pictures of the actual gel, according to an embodiment.

Reaction of Vinylsulfone-Modified Hyaluronic Acid with Dithiothreitol and the Preparation of in situ Hydrogel Vinylsulfone-modified hyaluronic acid was dissolved in an aqueous buffer solution, for example 0.1M, pH 7.4 phosphate buffer (PB), at various concentrations, at 7% w/v. Dithiolthreitol, which is a small molecule containing two thiols was dissolved in the same buffer solution at 0.1 mg/μL and added to the polymer solution at the molar ratio of 1:1/SH:VS. The gelation kinetics 1504 and pictures of the actual gel 1502 are shown in FIG. 15.

Reaction of Vinylsulfone-Modified Dextran with Dithiothreitol and the Preparation of in situ Hydrogel Vinylsulfone-modified dextran was dissolved in an aqueous buffer solution, for example 0.1M pH 7.4 phosphate buffer (PB), at various concentrations at 7% w/v. The crosslinker dithiothreitol was dissolved in the same buffer solution at 0.1 mg/μL and added to the polymer solution at the molar ratio of 1:1/SH:VS. The gelation kinetics 1506 and pictures of the actual gel 1508 are shown in FIG. 15.

Conjugating Reduced Glutathione on Vinylsulfone-Modified Hyaluronic Acid

Figure 16:
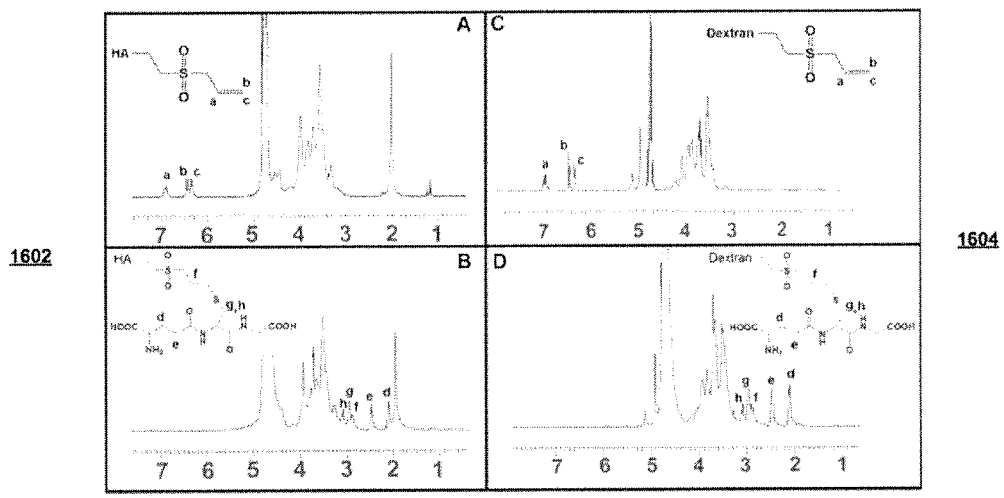
FIG. 16 is an exemplary non-limiting illustration of results of $^1$H NMR confirming the success of conjugation, according to an embodiment.

Vinylsulfone-modified hyaluronic acid was dissolved in an aqueous buffer solution, for example, 0.1M pH 7.4 PB, at 1% w/v. Two-time excessive (molar ratio to vinylsulfone group) glutathione was added to polymer solution. The reaction was carried out for 2 hours at room temperature and the produced was thoroughly dialysis and freeze dried. The success of conjugation was examined by $^1$H NMR, as shown in FIG. 16. Element 1602.

Conjugating Reduced Glutathione on Vinylsulfone-Modified Dextran

Vinylsulfone-modified dextran was dissolved in an aqueous buffer solution, for example, 0.1M pH 7.4 PB, at 1% w/v. Two-time excessive (molar ratio to vinylsulfone group) glutathione was added to polymer solution. The reaction was carried out for 2 hours at room temperature and the product was thoroughly dialyzed and freeze dried. The success of conjugation was examined by $^1$H NMR, as shown in FIG. 16, element 1604.

Compatibility of Vinylsulfone Grafted Polymer with a Rabbit Eye

To examine if the vinylsulfone group grafted on polymer is toxic to the eye, vinylsulfone grafted hyaluronic acid was used as an example. Vinylsulfone grafted hyaluronic acid was dissolved in PBS at 10% w/v and injected to the rabbit eye by intravitreal injection. The retina of the rabbit was examined using binocular indirect microscope (BIO).

Figure 17:
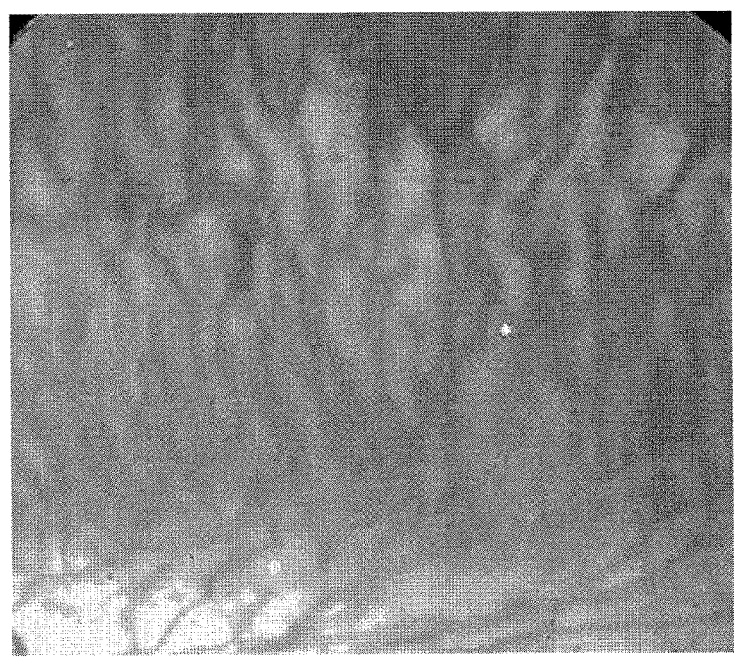
FIG. 17 is an exemplary non-limiting binocular indirect microscope image of peripheral rabbit retina after intravitral injection of 10% hyaluronic acid, according to an embodiment.

No hemorrhage, retinal detachment, edema, neovascularization or any other damages were observed both at day 7 and after 1 month. FIG. 17 shows a representative binocular indirect microscope image.

Crosslinking Vinylsulfone Grafted Polymers with Small Molecule Crosslinker

Polymers having two or more vinylsulfone groups per each molecule can be crosslinked by small molecules having two or more thiols. The following are examples of two vinylsulfone grafted polymers, vinylsulfone grafted hyaluronic acid and vinylsulfone grafted dextran crosslinked by a small dithiol molecule dithiothreitol at physiological pH.

It should be noted that this method is not limited to these two polymers and the particular crosslinking molecules we used, and the detail protocol used, for example, the specific buffer, pH, concentration, purification method, and the like, are merely examples.

Reaction of Vinylsulfone Grafted Hyaluronic Acid with Dithiothreitol and the Preparation of in situ Hydrogel Vinylsulfone grafted hyaluronic acid was dissolved in an aqueous buffer solution, for example 0.1M pH 7.4 phosphate buffer saline (PBS), at various concentrations.

Dithiolthreitol, which is a small molecule containing two thiols, was dissolved in the same buffer solution at 0.1 mg/μl and added to the polymer solution at the molar ratio of 1:1/SH:VS.

A hydrogel is formed shortly after mixing.

Reaction of Vinylsulfone Grafted Dextran with Dithiothreitol and the Preparation of in situ Hydrogel Vinylsulfone grafted dextran was dissolved in an aqueous buffer solution, for example PBS, at various concentrations. The crosslinker dithiothreitol was dissolved in the same buffer solution at 0.1 mg/µl and added to the polymer solution at the molar ratio of 1:1/SH:VS. A hydrogel was formed shortly after mixing.

Crosslinking Vinylsulfone Grafted Polymers with Thiol Containing Polymers

Polymers having two or more vinylsulfone groups per each molecule can be crosslinked by another large molecule, for example polymers, having two or more thiols per molecule. The following are examples of two VS grafted polymers: vinylsulfone grafted hyaluronic acid and vinylsulfone grafted dextran, crosslinked by two thiolated polymer thiolated hyaluronic acid (HA-SH) and thiolated dextran (dextran-VS).

It should be noted that this method is not limited to these two polymers, and the detailed protocol used, for example, the specific buffer, pH, concentration, purification method, and the like, are merely examples.

Synthesis of HA-SH

Vinylsulfone grafted hyaluronic acid was dissolved in a pH 7.4 buffer solution, for example 0.1M pH 7.4 phosphate buffer (PB), by 1% and purged with $N_2$. Equal molar dithiothreitol (DTT, molar ratio to OH groups of unmodified HA) was added to the reaction by aliquot previously dissolved in buffer solution. The pH is about 7.4 after adding dithiolthreitol.

The reaction was carried out for 30 minutes, stopped by readjusting pH to 4.5 by 1M HCl, and purified by diafiltration and freeze dried. The success of modification was monitored by the elimination of vinylsulfone double bond from $^1$H NMR spectrum and Ellman's assay.

Synthesis of Dextran-SH

Vinylsulfone grafted dextran (dextran-VS) was dissolved in a pH 7.4 buffer solution, for example 0.1M pH 7.4 phosphate buffer (PB), by 1% and purged with $N_2$. Equal molar dithiothreitol (DTT, molar ratio to OH groups of unmodified HA) was added to the reaction by aliquot previously dissolved in buffer solution. The pH is about 7.4 after adding DTT. The reaction was carried out for 30 minutes, stopped by readjusting pH to 4.5 by 1M HCl and purified by diafiltration and freeze dried. The success of modification was monitored by the elimination of vinylsulfone double bond from $^1$H NMR spectrum and Ellman's assay.

Reaction of Vinylsulfone Grafted Hyaluronic Acid with HA-SH and the Preparation of in situ Hydrogel Vinylsulfone grafted hyaluronic acid and HA-SH were dissolved separately in an aqueous buffer solution, for example PBS, at various concentrations, for example 10% w/v. Upon mixing, a hydrogel formed shortly.

Reaction of Vinylsulfone Grafted Dextran with Dextran-SH and the Preparation of in situ Hydrogel Vinylsulfone grafted dextran and dextran-SH were dissolved separately in an aqueous buffer solution, for example PBS, at various concentrations, for example 10% w/v. Upon mixing, a hydrogel formed shortly Reaction of Vinylsulfone Grafted Dextran with HA-SH and the Preparation of in situ Hydrogel Vinylsulfone grafted dextran and HA-SH were dissolved separately in an aqueous buffer solution, for example PBS, at various concentrations, for example 10% w/v. Upon mixing, a hydrogel formed shortly Encapsulating Macromolecules in the in situ Hydrogel and the in vitro Release The following is an example showing the controlled release of macromolecules from the hydrogel in vitro. A hyaluronic acid based hydrogel, either composed of vinylsulfone grafted hyaluronic acid crosslinked by small molecule crosslinker dithiothreitol or polymer crosslinker HA-SH, and three model proteins bovine serum albumin (BSA), near infrared labeled IgG (NIR-IgG) and Avastin, were used as a model polymer and macromolecule.

It should be noted that, the choice of polymer is highly dependent on the drug used. For example, Avastin is a full length antibody drug widely used for treating various eye diseases, including age-related macular degeneration. Avastint has molecular weight of 150 kDa and is positively charged at a neutral pH.

Thus, if desirable, a negatively charged polymer hyaluronic acid can be used to prolong the release of the drug.

When necessary, polymers of different charges can be mixed to give the most suitable release kinetics.

Hydrogel made from Vinylsulfone Grafted Hyaluronic acid Crosslinked with Dithiothreitol and the Release of BSA BSA was dissolved in a pH 7.4 buffer solution, at various concentration from 0.1% to 10% w/v. vinylsulfone grafted hyaluronic acid was dissolved in this protein solution. The crosslinker dithiothreitol was dissolved in the same buffer solution at 0.1 mg/µl and added to the vinylsulfone grafted hyaluronic acid/BSA solution at the molar ratio of 1:1/SH:VS.

Figure 18:
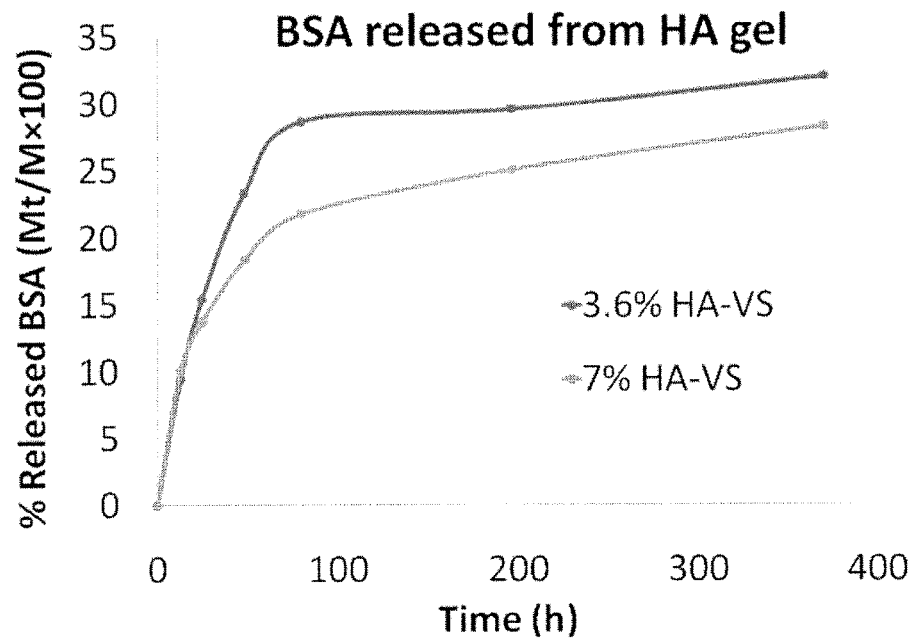
FIG. 18 is an exemplary non-limiting graph showing the in vitro release of antibody from a hyaluronic acid hydrogel, according to an embodiment.

Gel was formed after mixing, and the protein was encapsulated in the gel. PBS was then added as sink for the protein to release. Protein (BSA) release data for more than two months was shown in FIG. 18. Less than 30% of the protein was released.

Hydrogel made from Vinylsulfone Grafted Hyaluronic Acid Crosslinked with HA-SH and the Release of NIR-IgG and Avastin Vinylsulfone grafted hyaluronic acid and HA-SH was dissolved in PBS at separately. An antibody was added to the polymer right before mixing of the two polymers. After mixing, the polymer and drug mixture was incubated overnight to ensure complete gelation. PBS was then added as sink for the protein to release.

Figure 19:
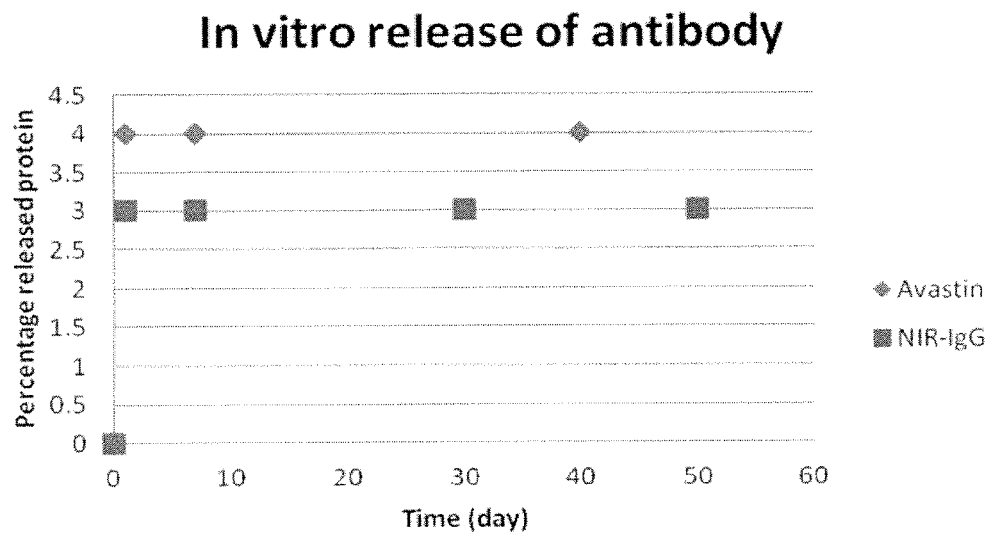
FIG. 19 is an exemplary non-limiting graph showing the in vitro release of antibody from a hyaluronic acid hydrogel, according to an embodiment.

Protein release data for more than one month was shown in FIG. 19. More than 95% of antibody was still retained in this gel, showing excellent controlled release property of this gel.

Encapsulating Drug-Encapsulated Particles in the Hydrogel

The following example shows how to encapsulate drug-encapsulated particles in the in situ hydrogel. The model drug molecule used is triamcinolone, a steroid drug widely used for treating various ocular inflammation.

It should be noted that this method is not limited to this particular drug, particular particle and particular vinylsulfone modified polymers and crosslinkers, and the detail protocol used, for example the specific buffer, pH, concentration, purification method, and the like, are only examples.

Model drug triamcinolone can be encapsulated in two component nanoparticles form by FTAEA and F-moc phenylalanine of diameter about 100 nm. The particles are dissolved in a pH 7.4 buffer solution.

Vinylsulfone grafted hyaluronic acid is dissolved a pH 7.4 buffer solution and mixed with the nanoparticle solution.

HA-SH dissolved in the same buffer solution as vinylsulfone grafted hyaluronic acid is added to vinylsulfone grafted hyaluronic acid/nanoparticle mixture. Gel was formed soon after mixing.

Ocular Compatibility of Hydrogel

The following are examples showing the biocompatibility of hydrogel in vivo. A hyaluronic acid based hydrogel was used as an example. However, it should be noted that, the choice of polymer and the detail protocol used, for example, the specific buffer, pH, concentration, purification method, and the like, are merely examples.

Figure 20:
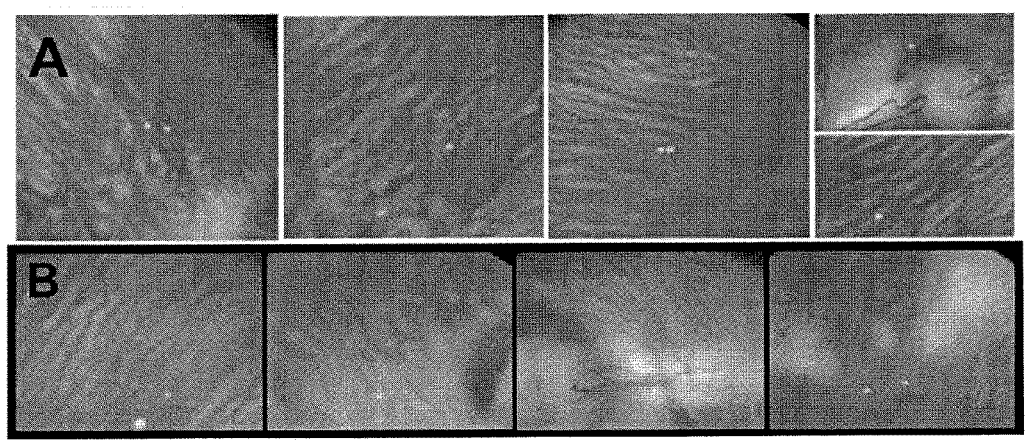
FIG. 20 shows exemplary non-limiting representative binocular indirect microscope images of the peripheral retina of the rabbit, showing no sign of hemorrhage, retinal detachment, edema, neovascularization, or other damage, according to an embodiment.

Vinylsulfone grafted hyaluronic acid and HA-SH were dissolved in PBS at separately. After mixing, 50 μl of the polymer mixture was injected to the rabbit eye by intravitreal injection. The injected eyes were examined by binocular indirect microscope periodically. No hemorrhage, retinal detachment, edema, neovascularization or any other damages were observed in any ocular examination. Representative binocular indirect microscope images are shown in FIG. 20.

Injection of Protein Encapsulated in situ Hydrogel into a Rabbit Eye

The following are examples showing the injection of hydrogel into the rabbit eye and the controlled release of drug from the hydrogel in vivo. A hyaluronic acid based hydrogel and NIR-IgG, which is structurally similar to a widely used anti-VEGF antibody, Avastin, for treating eye diseases, was used as model polymer and drug molecule. However, it should be noted that, the choice of polymer is highly dependent on the drug used, and the detail protocol used, for example the specific buffer, pH, concentration, purification method, and the like, are merely examples.

Sub-Tenon's Injection of Protein Encapsulated Hyaluronic Acid in situ Hydrogel

Figure 21:
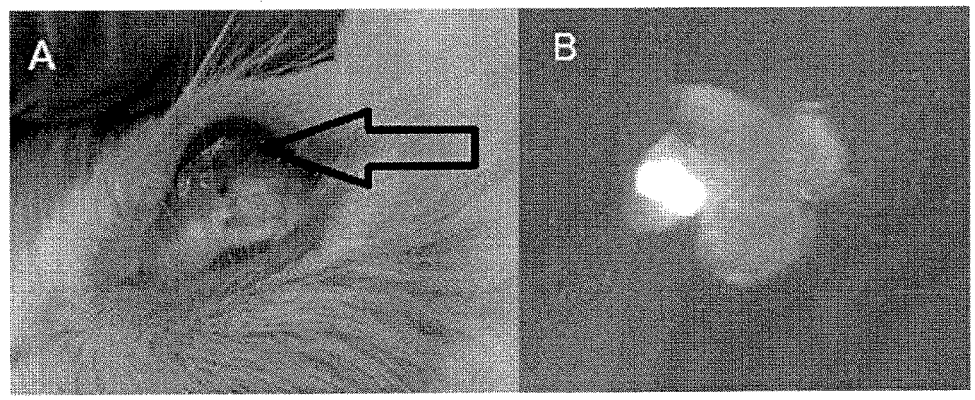
FIG. 21 is an exemplary non-limiting illustration of sub-Tenon's injection of polymers into the rabbit eye, according to an embodiment.

Vinylsulfone grafted hyaluronic acid and HA-SH were dissolved in PBS at separately. NIR-IgG was added right before mixing of the two polymers. After mixing, 600 μl of the polymer/drug mixture was injected to the rabbit eye by sub-Tenon's injection (shown in FIG. 21(A)).

One week later, the rabbit was enucleated and the gel was removed from the sub-Tenon's space. The presence of NIR-IgG in the sclera was examined by NIR fluorescence imager. The fluorescence in the sclera of the treated eye indicates the release of drug in vivo in FIG. 21(B).

Intravitreal Injection of Protein Encapsulated Hyaluronic Acid in situ Hydrogel

Vinylsulfone grafted hyaluronic acid and HA-SH were dissolved in PBS separately. An antibody was added to the polymer right before mixing of the two polymers.

After mixing, 50 μl of the polymer/drug mixture was injected to the rabbit eye by intravitreal injection. One week later, the rabbit was killed and enucleated. The eye was bisected and the presence of NIR-IgG inside the eye was examined by NIR fluorescence imager.

Figure 22:
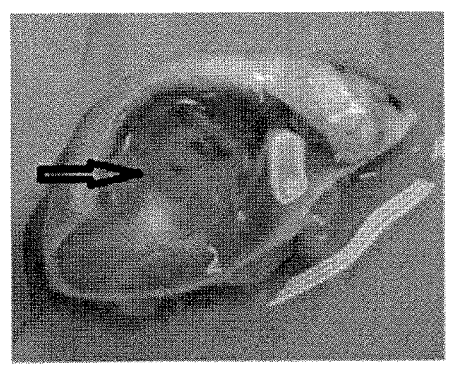
FIG. 22 is an exemplary non-picture taken 1 week after intravitreal injection of NR-IgG encapsulated hydrogel with the arrow indicating the location of the hydrogel, according to an embodiment.

FIG. 22 is a picture of the bisected rabbit eye ball. A transparent hydrogel is clearly seen surrounded by the vitreous.

Figure 23:
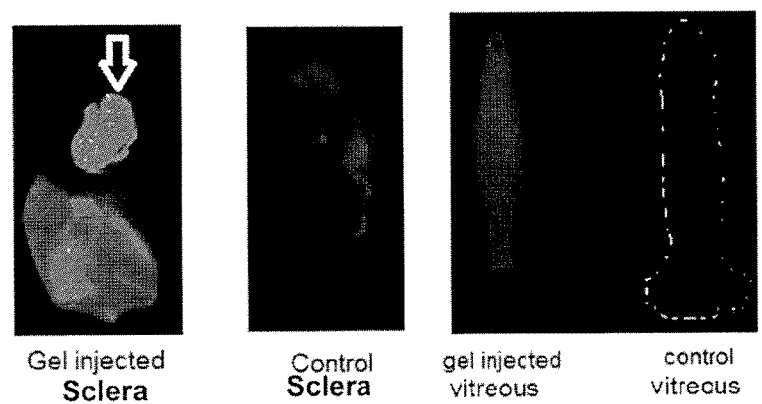
FIG. 23 is an exemplary non-limiting comparison of the fluorescence in sclera and vitreous of treated and control eye, according to an embodiment.

FIG. 23 shows the comparison of vitreous from treated eye and control eye. The fluorescence in the vitreous of treated eye indicates the release of drug in vivo.

What has been described above includes examples of the embodiments of the subject disclosure. It is, of course, not possible to describe every conceivable combination of components or methods for purposes of describing the claimed subject matter, but it is to be appreciated that many further combinations and permutations of the various embodiments are possible. Accordingly, the claimed subject matter is intended to embrace all such alterations, modifications, and variations that fall within the spirit and scope of the appended claims. While specific embodiments and examples are described in this disclosure for illustrative purposes, various modifications are possible that are considered within the scope of such embodiments and examples, as those skilled in the relevant art can recognize.

In addition, the words "example" or "exemplary" are used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

In addition, while an aspect may have been disclosed with respect to only one of several embodiments, such feature may be combined with one or more other features of the other embodiments as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Numerical data, such as temperatures, concentrations, times, ratios, and the like, are presented herein in a range format. The range format is used merely for convenience and brevity. The range format is meant to be interpreted flexibly to include not only the numerical values explicitly recited as the limits of the range, but also to include all the individual numerical values or sub-ranges encompassed within the range as if each numerical value and sub-range is explicitly recited. When reported herein, any numerical values are meant to implicitly include the term "about." Values resulting from experimental error that can occur when taking measurements are meant to be included in the numerical values.

What is claimed is:

1. A drug delivery system, comprising:
    a first molecule having a first structure, wherein the first molecule is a multi-vinylsulfone containing polysaccharide, wherein the polysaccharide of the multi-vinylsulfone containing polysaccharide is linked to the vinylsulfone groups via an ether linkage;
    a second molecule having a second structure different from the first structure, wherein the second molecule is a multi-thiol containing polysaccharide; and
    a therapeutic agent;
    wherein the first molecule and the second molecule form a hydrogel in which the first molecule is a backbone of the hydrogel, the second molecule is a backbone of the hydrogel, and the first and second molecules are cross-linked to each other.

2. The drug delivery system of claim 1, wherein the hydrogel is formed when the first molecule forms a covalent bond with the second molecule.

3. The drug delivery system of claim 2, wherein the therapeutic agent is encapsulated within a network formed by the first molecule and the second molecule.

4. The drug delivery system of claim 1, wherein the therapeutic agent is a biomacromolecule or a particle encapsulating a drug molecule.

5. The drug delivery system of claim 1, wherein the drug delivery system is administered to the body by an intravitreal injection, a peribulbar injection, or a sub-Tenon injection.

6. The drug delivery system of claim 1, wherein
the hydrogel is formed in situ, and
the therapeutic agent is released from the hydrogel by diffusion of the therapeutic agent from the hydrogel or by degradation of the hydrogel.

7. The drug delivery system of claim 1, wherein the drug delivery system is administered to the body by a periocular injection or an intraocular injection,
wherein the periocular injection is a subconjunctival injection, a retrobulbar injection, a peribulbar injection, or a sub-Tenon injection, and
wherein the intraocular injection is an intravitreal injection, an injection to the anterior chamber of the eye, an injection to the posterior chamber of the eye, or an injection to the lens or lens capsule.

8. The drug delivery system of claim 1, wherein the first molecule is active towards the second molecule at mild aqueous conditions.

9. The drug delivery system of claim 1, wherein the polysaccharide of the multi-thiol containing polysaccharide is hyaluronic acid (HA), dextran, alginate, or cyclodextrin.

10. The drug delivery system of claim 1, wherein the polysaccharide of the multi-thiol containing polysaccharide is HA, dextran, or a combination thereof.

11. The drug delivery system of claim 10, wherein the polysaccharide of the multi-vinylsulfone containing polysaccharide is HA.

12. The drug delivery system of claim 1, wherein the polysaccharide of the multi-vinylsulfone containing polysaccharide is HA, dextran, alginate, or cyclodextrin.

13. A method of forming a hydrogel, the method comprising:

dissolving a water soluble polysaccharide in an aqueous solution to form a polymer solution;
adding a molecule containing at least two vinylsulfone groups to the polymer solution; and forming a multi-vinylsulfone containing polysaccharide by controlling a number of the vinylsulfone groups that are grafted on the polysaccharide, wherein the vinylsulfone groups grafted on the polysaccharide are chemically reactive, and wherein the polysaccharide of the multi-vinylsulfone containing polysaccharide is linked to the vinylsulfone groups via an ether linkage; and
cross-linking the multi-vinylsulfone containing polysaccharide to a multi-thiol containing polysaccharide to form the hydrogel,
where the multi-vinylsulfone containing polysaccharide is a backbone of the hydrogel, the multi-thiol containing polysaccharide is a backbone of the hydrogel, and the multi-vinylsulfone containing polysaccharide and multi-thiol containing polysaccharide are cross-linked to each other.

14. The method of claim 13, wherein the dissolving further comprises dissolving the water soluble polymer in the aqueous solution comprising a salt or an organic solvent.

15. The method of claim 13, wherein the dissolving further comprises dissolving the water soluble polymer in an alkaline aqueous solution.

16. The method of claim 13, wherein the controlling comprises varying a reaction time, an amount of molecules containing the at least two vinylsulfone groups, or a basicity of the aqueous solution.

17. The method of claim 13, wherein the polysaccharide of the multi-thiol containing polysaccharide is HA, dextran, alginate, or cyclodextrin.

18. The method of claim 13, wherein the polysaccharide of the multi-thiol containing polysaccharide is HA, dextran, or a combination thereof.

19. The drug delivery system of claim 18, wherein the polysaccharide of the multi-vinylsulfone containing polysaccharide is HA.

20. The drug delivery system of claim 13, wherein the polysaccharide of the multi-vinylsulfone containing polysaccharide is HA, dextran, alginate, or cyclodextrin.

* * * * *